United States Patent [19]

Takechi et al.

[11] 4,104,125

[45] Aug. 1, 1978

[54] PROCESS FOR PRODUCING HUMAN LYSOZYME

[75] Inventors: Kazuo Takechi, Sakai; Tsuyoshi Takahashi, Osaka; Toyoaki Inaba, Nagaokakyo; Eiichi Hasegawa, Kyoto, all of Japan

[73] Assignee: The Green Cross Corporation, Osaka, Japan

[21] Appl. No.: 815,359

[22] Filed: Jul. 13, 1977

[30] Foreign Application Priority Data

Feb. 28, 1977 [JP] Japan ................................. 52/20984

[51] Int. Cl.$^2$ ............................................ C07G 7/026
[52] U.S. Cl. ............................... 195/66 R; 260/112 B
[58] Field of Search ................... 23/230 B; 195/66 R; 260/112 B

[56] References Cited

U.S. PATENT DOCUMENTS

| | | | |
|---|---|---|---|
| 2,705,230 | 3/1955 | Reid | 260/122 |
| 2,765,299 | 10/1956 | Porsche | 260/122 |
| 2,958,628 | 11/1960 | Hink, Jr. | 260/112 B X |
| 3,850,903 | 11/1974 | Garcia | 260/112 B |
| 3,859,435 | 1/1975 | Bruzzese | 23/230 B X |
| 3,926,939 | 12/1975 | Ivanov | 260/122 |
| 3,940,317 | 2/1976 | Katz | 195/66 R |
| 4,017,470 | 4/1977 | Izaka | 260/112 B |

FOREIGN PATENT DOCUMENTS 1,441,752  7/1976  United Kingdom.

OTHER PUBLICATIONS

Chemical Abstracts, 70: 9066d (1969).
Chemical Abstracts, 73: 36084b (1970).
Chemical Abstracts, 77: 86595x (1972).
Chemical Abstracts, 82: 166992 (1975).
Chemical Abstracts, 83: 143697g (1975).
Science, 155, 1536–1537, (Mar. 24, 1967).

*Primary Examiner*—Sidney Marantz
*Attorney, Agent, or Firm*—Cushman, Darby & Cushman

[57] ABSTRACT

It has been discovered that lysozyme in the blood is concentrated into the albumin fraction when the blood is fractionated by the alcohol fractionation method at lowered temperature or the ammonium sulfate fractionation method. Lysozyme can be produced by contacting the albumin fraction with a weakly acidic cation-exchanger such as CM-cellulose to adsorb selectively the lysozyme with the cation-exchanger and then eluting the lysozyme adsorbed from the cation-exchanger.

16 Claims, 1 Drawing Figure

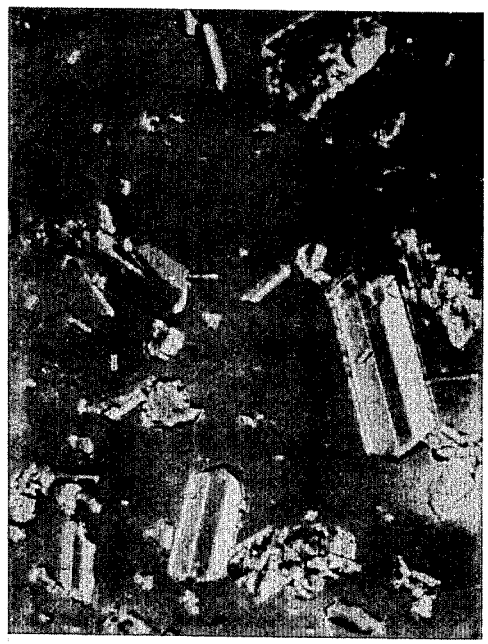

PROCESS FOR PRODUCING HUMAN LYSOZYME

This invention relates to a process for producing human lysozyme. More particularly, it related to a process for producing lysozyme from albumin fraction of human blood.

"Lysozyme" is a general term for the enzymes which catalyze the hydrolysis of mucopolysaccharide present in the cell wall of micro-organisms and thereby dissolve them. In albumen white of fowl egg the content of lysozyme is as high as 3% based on the total protein, so that lysozyme preparations have predominantly been produced from the white of hen eggs. On the other hand, lysozyme is found also in the human body fluids such as tear, nasal mucus, blood and urine, although the content is quite low except tear. A higher content of lysozyme is found in the body fluids of leukemic patients. In 1967, Osserman isolated for the first time the human lysozyme in a crystalline form from the urine of the patients of monocytic leukemia by means of adsorption onto bentonite (Osserman: Science, 155, 1536–1537 (1967)).

Since the lysozyme isolated from the white of egg is a heterogeneous protein in a human body, it is restricted in dose and route of administration when being given to a human as a medicine. In addition, its enzymatic activity is said to be one-half to one-third lower than that of human lysozyme. However, the amount of lysozyme contained in the available body fluids or tissues of normal human is quite little. For example, its content in the normal human blood is so low as 2–10 ppm. At the present time, its efficient separation and recovery from normal human blood is not practised commercially. For all that, it is a matter of course that neither of tears and nasal mucus, nor the urines of leukemic patients, can be utilized as a source of lysozyme commercially.

It is the object of this invention to provide an efficient process for separating lysozyme from human blood and purifying it.

The present inventors conducted an extensive study with the aim of accomplishing the object mentioned above. As the result, they discovered an unexpected fact that lysozyme was able to be concentrated into the albumin fraction of blood. The inventors also discovered that the lysozyme could be isolated from the albumin fraction by a simple procedure.

Thus, according to this invention there is provided a process for producing human lysozyme which comprises fractionating the components of human blood by solubility difference to collect the albumin fraction, contacting the albumin fraction with a weakly acidic cation-exchanger to let the exchanger adsorb the lysozyme present in the albumin fractions, desorbing the adsorbed lysozyme, and recovering the desorbed lysozyme.

The human blood used in the process of this invention is preferably a normal human blood which includes the blood present in the placental tissue and the retroplacental blood. It is well known that the albumin fraction can be separated from said human blood according to the fractionating method by the utilization of solubility difference, which method is based mainly on the ammonium sulfate fractionation or the Cohn's low temperatura alcohol fractionation. According to the ammonium sulfate fractionation method, the albumin fraction in the blood is collected in the form of precipitates which are formed when the concentration of ammonium sulfate is in the range of 45 to 75% saturation. According to the Cohn's low temperature alcohol method, the albumin fraction in the blood is collected as fractions IV-1 and V. These fractions are purified and sold as an albumin preparation. A number of techniques for modifying or improving the fractionating and purifying processes have been mentioned in papers. They are, for example and in brief, (1) from plasma or serum: a technique which comprises subjecting the supernatant of Cohn's IV-1 fraction again to fractionation with an ethanol concentration of 25 to 38% (U.S. Pat. No. 2,958,628); a technique which comprises removing impure proteinous substances such as lipoprotein from the fraction IV-1 by using organic acids and acrinol (U.S. Pat. No. 4,017,470); a technique which comprises recovering albumin from the precipitate of fraction IV-4 (U.S. Pat. No. 3,850,903); a technique which comprises adding a fatty acid to an aqueous solution containing albumin, heating the resulting mixture and then recovering a purified albumin (U.S. Pat. Nos. 2,765,299 and 2,705,230); (2) from placenta: a technique which comprises treating a liquid extract of placenta successively with citric acid, phenol and sodium carbonate to remove impurities and then recovering albumin (Japanese Patent Publication No. 7762/1973); a technique which comprises fractionating a liquid extract of placenta with ammonium sulfate, adding butyric acid to the fraction, heating it and then recovering albumin from the supernatant (Japanese Patent Publication No. 16041/1968); a technique which comprises employing an alcohol and a salt of fatty acid in place of the butyric acid in the last technique (U.S. Pat. No. 3,926,939); a technique which comprises employing mandelic acid or caproic acid and ethylenediaminetetraacetic acid in its place (Japanese Patent Kokai (Laid-Open) No. 88621/1976); a technique which comprises employing mandelic acid in its place (Japanese Patent Publication No. 40132/1976) and a technique which comprises employing caprylic acid and chloroform in its place (British Pat. No. 1,441,752).

The processes above can all be used for obtaining the albumin fraction used in the present invention. Among them the processes disclosed in U.S. Pat. Nos. 4,017,470 and 2,958,628 are preferable when the raw material is plasma or serum. And, in case of placenta source, a process comprising a step of heating the albumin fraction from placenta source in the presence of an organic acid having 4 to 8 carbon atoms to remove impure proteinous substances, is recommendable, which process is disclosed above.

More particularly, the processes claimed in U.S. Pat. Nos. 4,017,470 and 2,958,628 are respectively as follows:

"A method for preparing a heat-stable plasma protein solution showing no blood pressure-depressing action which comprises adding distilled water to a paste IV-1, a fraction obtained from the Cohn's cold ethanol plasma fractionation method, to extract water-soluble proteins in the paste and removing solids contained in the mixture by centrifuging to obtain an extract containing water-soluble proteins, heat treating the resulting extract at pH 4.5 to 5.5 at 50° to 65° C with an organic acid having 4 to 8 carbon atoms to a final concentration of the organic acid of 2 to 6 W/V %, removing as precipitates by filtration or centrifugation lipo- and glycoproteins contained in the extract, adding 2-ethoxy- 6,9-diaminoacridine lactate in an amount of 0.2 to 3.0 g per liter of the supernatant to the resulting supernatant, allowing the mixture to stand at room temperature or below and removing by precipitation residual lipo-proteins giving turbidity to the supernatant, and then removing blood pressure-depressing substances present in the resulting supernatant by adsorption with an inorganic adsorbent or cation exchanger."

and

"In the process of fractionating human plasma proteins by fractional precipitation with cold ethanol, after the removal of all coagulation components and all gamma globulin, the step of precipitating a mixture of albumin, alpha globulin and beta globulin at an ethanol concentration of 25 to 38%, a pH of 4.3 to 4.7, a temperature of between −2° C and the freezing point of the solution, an ionic strength of less than 0.12, and a protein concentration of greater than 2.2 percent."

As an example of the preferable process in case of the placenta source, there is mentioned the translation of claim of Japanese Patent Publication No. 40,132/76 as follows:

"A process for recovering a heat-stable human plasma protein from the human placenta or retroplacental blood, characterized by using as a raw material human placenta or retroplacental blood which have been frozen and reserved immediately after its delivery, separating gamma-globlin from the blood component solution fractionated from the raw material to obtain a supernatant, adding to the supernatant solid mandelic acid or a solution thereof till the solution contains the acid at a concentration of 2.5–5.0%, maintaining the pH of the reaction solution at 4.4–5.5, heating the solution at 58°–62° C, removing all of precipitates formed and recovering the objective substance from the supernatant."

In this invention, the albumin fraction mentioned above or its purified preparation can be utilized effectively. This is owing to the inventors' discovery that throughout the fractionation of blood by solubility difference lysozyme behaves just in the same manner as albumin and both the ingredients are concentrated into albumin fractions. No worker has even been aware of this behavior of lysozyme, and the concentrated lysozyme has been overlooked as a mere impurity in albumin preparation.

The process for recovering lysozyme according to this invention comprises fractionating human plasma, human serum or blood derived from human placenta such as extract of human placenta or human retroplacental blood to isolate albumin fractions therefrom by solubility difference, contacting the isolated albumin fractions with a weakly acidic cation-exchanger to have lysozyme adsorbed on the exchanger, desorbing the adsorbed lysozyme, and recovering the desorbed lysozyme.

When this process is combined with a process for obtaining an albumin preparation, there can be obtained lysozyme together with a further purified albumin, which is one of the characteristic features of this invention. Accordingly, the starting material used in this invention is preferably a purified solution of albumin fraction which is not yet sterilized, filtered, dried and formed into a preparation. The solution contains an albumin, having a purity of 50 to 97% based on the total protein.

The weakly acidic cation-exchangers preferably usable in this invention include carboxymethyl cellulose (CM-cellulose), phospho-cellulose (p-cellulose), carboxymethyl Sephadex (CM- Sephadex ® which is carboxymethyl-crosslinked dextran manufactured by Pharmacia Co., Sweden), and the like. Said solution is contacted with said cation-exchanger at a pH value of 5–10, preferably 7–9. pH values of said albumin fraction solution and said cation-exchanger are adjusted to the above-mentioned range preferably by the use of a buffer solution, such as 0.02 M phosphate buffer solution. They may be contacted together either by merely mixing them together or by passing said albumin fraction solution through a column packed with said cation-exchanger. By this procedure, the lysozyme in the solution is completely adsorbed on the cation-exchanger, while the albumin remains in the solution in a further purified state. The cation-exchanger which has adsorbed the lysozyme is preferably washed with the same buffer solution as above, after which the lysozyme is eluted from the cation-exchanger in the usual manner with an eluent such as an alkaline solution (pH 10–12), a highly concentrated solution of inorganic neutral salt (for example, about 5–15% solution of sodium chloride) or an aqueous solution of an inorganic neutral salt having a concentration of about 5 to 15% and a pH value of 8 to 10.

Though the conditions other than the above in the adsorption and desorption procedures are not particularly limited, the temperature used may be an ambient temperature of 3°–20° C, and the quantity of said weakly acidic cation-exchanger used is usually in the range of about 30–100 milliliters per one liter of a starting solution containing 3–10% (W/V) of albumin.

The concentration of lysozyme in the eluate is evaluated by measuring $OD_{280\ nm}$ with respect to protein content and by the turbidimetry (Proc. Soc. Exp. Biol. Med., 119, 384–386 (1965)) with respect to lysozyme titer. The eluate is dialyzed against water for 10–20 hours till the inorganic salts have almost been eliminated. Subsequently, its pH value is adjusted to 5.0–6.0 and, if necessary, it is heat-treated at 60° C for 10 hours for the purpose of inactivating the hepatitis vira (lysozyme is resistant to a high temperature of this extent), after that it is sterilized and filtered to give a solution of injectable lysozyme preparation. Finally, the solution may be freeze-dried to give a solid bulk of lysozyme preparation.

The lysozyme preparation thus obtained has a purity of 60% or more and can directly be employed as an intra-venous, intra-arterial or an intra-muscular injection. Of course, it may also be administered to human body in the form of collyrium, aerosol or oral preparation. It may be administered at any time without occurrence of allergic reaction at a dose of 0.1–20 mg titer per one kilogram of body weight when used as an injection and at a dose of 0.2–10 mg titer/milliliter when used as an artificial tear or a collyrium.

It is also possible to obtain a crystalline lysozyme by an additional purification of the lysozyme preparation mentioned above. That is, a crystalline lysozyme can be obtained by gel-filtering the lysozyme solution with crosslinked dextran (for example, Sephadex G-50 ® manufactured by Pharmacia Co., Sweden) at a pH value of 5–6 to enhance the purity of lysozyme up to 90%, dialyzing the purified solution against sodium chloride solution (pH 4–5) and then concentrating the dialyzed solution. The accompanying photograph illustrates a magnified view ( × 400) of the crystal thus obtained.

The human lysozyme produced according to this invention can be orally administered to patients having those diseases to which the usual lysozyme preparations derived from egg white is applicable. Also, the human lysozyme produced according to this invention can effectively be administered by injection, and thus the scope of applicability of the preparation can be expanded. For example, lysozyme can be let act upon a bacterial focus of suppuration in the body by injecting it directly into the focus or via the artery. It is also possible to let an asthmatic patient inhale the lysozyme preparation of this invention at a high concentration in order to eliminate the sputum capable of obstructing the bronchiole at the time of asthmatic attack, by which the attack can be ameriolated without any allergic reaction and sometimes the patient can be saved from asthmatic death.

According to the process of this invention, a human lysozyme preparation which has never been commercialized so far can be obtained in high purity by applying the blood fractionation process utilizing solubility difference, which forms the staple of the conventional processes for the production of human albumin preparations. Furthermore, the process of this invention has a subsidiary merit that albumin fraction can be obtained in a further purified form. For these reasons, the process of this invention is quite valuable from the commercial point of view.

The denotation "% (W/V)" in this specification and claims shows the concentration of a solute in a solution in the proportion of the solute in weight unit and the solution in volume unit.

Details of this invention will be illustrated by the following examples to which the present invention is not limited.

EXAMPLE 1

Ten liters of a thermally stable plasma protein solution (protein content 600 g; chemical composition of the protein: albumin 95%, α- and β-globulins 4%, proteins which transferred from γ-region to cathode 1%) which had been obtained from the placental blood according to the procedure mentioned in Example of Japanese Patent Publication No. 40132/1976 was regulated to a pH value of 7.0 ± 0.05 with 1N-NaOH solution. The solution of thermally stable plasma protein was passed through a column packed with 100 g of CM-cellulose (manufactured by Seikagaku Kogyo K.K.) preliminarily washed thoroughly and adjusted to a pH value of 7.0 ± 0.05. The passing fraction was an albumin fraction, of which $OD_{280\ nm}$ was determined. It had nearly the same protein content as was found before passage through the column, so that more than 99% of the protein passed the column without adsorption. The passing fraction contained no lysozyme at all, indicating that lysozyme was completely adsorbed by the CM-cellulose. In order to eliminate the albumin remained in the column, the latter was washed with about 1,000 ml of 0.02 M tris-(hydroxymethyl)aminomethane-hydrochloric acid (pH 9.0) and then with about 1,000 ml of 0.02 M tris-(hydroxymethyl)aminomethane-hydrochloric acid containing 0.13 M of NaCl (pH 9.0) successively. Subsequently, 0.02 M tris-(hydroxymethyl)aminomethane-hydrochloric acid containing 15% of NaCl (pH 9.0) was passed through the column to elute the adsorbed lysozyme. The eluted lysozyme had a purity of about 80%. The eluate was dialyzed against running water, sterilized, filtered, divided into vials and freeze-dried. The lysozyme preparation in vial thus obtained had a specific activity of 3.2 mg titer/mg and a total protein content of 1.6 mg. The total yield is 208 mg.

EXAMPLE 2

Ten liters of a thermally stable plasma protein (protein content 500 g; chemical composition of the protein: albumin 87.0%, α-globulin 8.4%, β-globulin 3.6%, other proteins which transferred from γ-region to cathode 1%) obtained from Cohn's supernatant fraction IV-1 of human plasma according to the procedure mentioned in U.S. Pat. No. 2,958,628 was regulated to a pH value of 7.0 ± 0.05 with 1N-NaOH solution. On the other hand, 600 ml of p-cellulose (manufactured by Seikagaku Kogyo K.K.) which had preliminarily been washed with water thoroughly and equilibrated at a pH value of 7.0 ± 0.05 with 0.02 M phosphate buffer solution was packed into a column, through which was passed the thermally stable plasma protein solution mentioned above. Albumin contained in the solution passed without being adsorbed. Thereafter, the column was washed with the same buffer solution as used above for equilibration and then with 0.02 M tris-(hydroxymethyl)aminomethane-hydrochloric acid containing 0.13 M of NaCl successively to eliminate albumin from the column completely. Subsequently, 0.02 M tris-(hydroxymethyl)aminomethane-hydrochloric acid containing 8% of NaCl (pH 8.5) was passed through the column to elute the adsorbed lysozyme. The eluate is collected, dialyzed against running water, sterilized, filtered, divided into vials and freeze-dried. The lysozyme preparation in vial thus obtained had a purity of 60%, a specific activity of 2.4 mg titer/mg and a total protein content of 2.1 mg. The total yield is 30 mg.

EXAMPLE 3

Lysozyme was recovered in the same manner as in Example 1 from 10 liters of a plasma protein mainly composed of albumin (chemical composition of the protein: albumin 95%, α- and β-globulins 4%, other proteins which transferred from γ-region to cathode 1%) which had been recovered from the precipitate of Cohn's fraction IV-1 according to the process mentioned in Example 1 of U.S. Pat. No. 4,017,470. The lysozyme preparation in vial obtained had a purity of 65%, with a specific activity of 2.6 mg titer/mg and a total protein content of 1.9 mg. The total yield is 28 mg.

EXAMPLE 4

Lysozyme was recovered in the same manner as in Example 1 from 10 liters of a thermally stable plasma protein which had been obtained by heating the fraction obtained from placental blood at 60° C for about one hour at a pH value of 4.8 in the presence of 4% (W/V) of mandelic acid and 1 mM of EDTA according to the process mentioned in Example 1 of Japanese Patent Kokai (Laid-Open) No. 88,621/1976 and thereby eliminating therefrom a precipitate containing hemoglobin and alkaline phosphatase. The chemical composition of the starting protein was as follows: albumin 95%, α- and β-globulins 4%, other proteins which transferred from γ-region to cathode 1%. The lysozyme preparation in vial obtained had a purity of 70% with a specific activity of 2.8 mg titer/mg and a total protein content of 1.8 mg. The total yield is 150 mg.

EXAMPLE 5

A 5% aqueous solution of lysozyme obtained according to the procedure of Example 1 (specific activity 3.2 mg titer/mg; total protein content 208 mg) was gel-filtered at a pH value of 5.5 with Sephadex G-50 ®. The filtrate was concentrated and dialyzed against 5% aqueous solution of NaCl having a pH value of 4.5. Thus, the lysozyme was obtained in a crystalline form. The accompanying photograph illustrates a magnified view ($\times$ 400) of the crystal obtained.

What is claimed is:

1. A process for producing a human lysozyme preparation which comprises fractionating a human blood by solubility difference to isolate an albumin fraction, contacting said albumin fraction with a weakly acidic cation-exchanger to adsorb the lysozyme contained in said albumin fraction and desorbing the adsorbed lysozyme.

2. A process according to claim 1, wherein said albumin fraction is human plasma, human serum or a human placental blood.

3. A process according to claim 1, wherein said albumin fraction contains an albumin having a purity of 50 to 97% based on the total protein.

4. A process according to claim 1, wherein said albumin fraction is Cohn's fraction IV-1.

5. A process according to claim 1, wherein the fractionation is carried out by adding distilled water to a paste IV-1, a fraction obtained from the Cohn's cold ethanol plasma fractionation method, to extract water-soluble proteins in the paste and removing solids contained in the mixture by centrifuging to obtain an extract containing water-soluble proteins, heat treating the resulting extract at pH 4.5 to 5.5 at 50° to 65° C with an organic acid having 4 to 8 carbon atoms to a final concentration of the organic acid of 2 to 6 W/V%, removing as precipitates by filtration or centrifugation lipo- and glyco-proteins contained in the extract, adding 2-ethoxy-6,9-diaminoacridine lactate in an amount of 0.2 to 3.0 g per liter of the supernatant to the resulting supernatant, allowing the mixture to stand at room temperature or below and removing by precipitation residual lipo-proteins giving turbidity to the supernatant, and then removing blood pressure-depressing substances present in the resulting supernatant by adsorption with an inorganic adsorbent or cation exchanger.

6. A process according to claim 1, wherein the fractionation is carried out by precipitating a mixture of albumin, alpha globulin and beta globulin at an ethanol concentration of 25 to 38%, a pH of 4.3 to 4.7, a temperature of between $-2°$ C and the freezing point of the solution, an ionic strength of less than 0.12, and a protein concentration of greater than 2.2 percent.

7. A process according to claim 1, wherein the fractionation is carried out by the process comprising heating the albumin fraction obtained from placenta source in the presence of an organic acid having 4 to 8 carbon atoms to precipitate and remove impure proteinous substances.

8. A process according to claim 1, wherein said weakly acidic cation-exchanger is carboxymethyl cellulose, phospho-cellulose or carboxymethyl-crosslinked dextran.

9. A process according to claim 1, wherein said contact is carried out at a pH value of 5 to 10.

10. A process according to claim 1, wherein said contact is carried out at a pH value of 7 to 9.

11. A process according to claim 1, wherein said desorption is carried out at a pH value of about 10 to 12.

12. A process according to claim 1, wherein said desorption is carried out in an aqueous solution of an inorganic neutral salt having a concentration of about 5 to 15%.

13. A process according to claim 1, wherein said desorption is carried out in an aqueous solution of an inorganic neutral salt having a concentration of about 5 to 15% and a pH value of 8 to 10.

14. A process according to claim 1, wherein the solution of desorbed material is heated at 60° C for 10 hours.

15. A process according to claim 1, wherein the solution of desorbed material is gel-filtered and concentrated to crystallize the lysozyme contained therein.

16. A process according to claim 15, wherein the solution of desorbed material is gel-filtered with cross-linked dextran.

* * * * *